United States Patent [19]

Floyd et al.

[11] 4,028,846

[45] June 14, 1977

[54] PLANT TREATMENT

[76] Inventors: John Francis Leslie Floyd; James Robert Charles Elliott, both of 3 Woodside Ave., Chesham Bois Amersham, Buckinghamshire, England

[22] Filed: Jan. 13, 1976

[21] Appl. No.: 648,718

[52] U.S. Cl. .................................. 47/57.5; 21/73
[51] Int. Cl.² ......................................... A01G 29/00
[58] Field of Search .................... 47/57.5; 21/73

[56] References Cited

UNITED STATES PATENTS

| 1,756,453 | 4/1930 | Davey et al. ....................... 47/57.5 |
| 2,874,658 | 2/1959 | De Jarnette et al. ............ 47/57.5 X |
| 3,124,904 | 3/1964 | Mauget ............................... 47/57.5 |
| 3,130,519 | 4/1964 | Mauget ............................... 47/57.5 |
| 3,295,254 | 1/1967 | Schoonman ........................ 47/57.5 |

*Primary Examiner*—Robert E. Bagwill
*Attorney, Agent, or Firm*—Kemon & Estabrook

[57] ABSTRACT

Substances for combatting diseases and pests in plants are injected into the body of the plant from an aerosol generating device. The droplets then disperse through the body of the plant.

2 Claims, 1 Drawing Figure

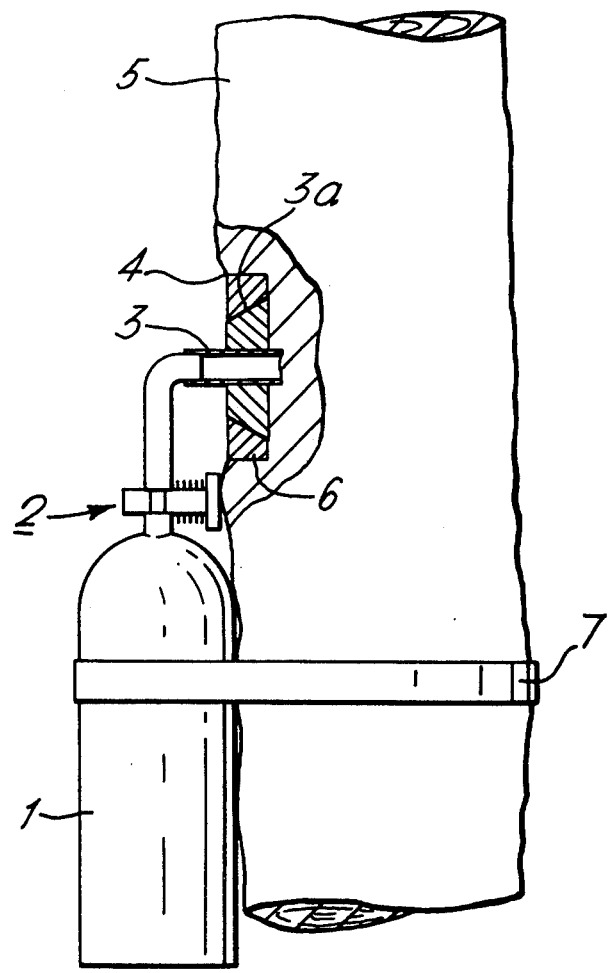

PLANT TREATMENT

This invention relates to a method of treating plants, particularly but not exclusively trees, in order to combat disease or pest infestation.

Plants are liable to attack by a variety of diseases and/or pests; for example elm trees in the United Kingdom are being killed by a disease, introduced by a beetle, known as "Dutch elm disease".

Various chemical compounds for treating for various diseases and pests are well-known, but a common difficulty is the difficulty in applying the chemical compound to the plant to be treated.

It is known to spray the chemical compound over a plant to be treated, and also, for example when treating a tree infected with Dutch elm disease, to inject a plant to be treated with the chemical compound or a solution thereof.

However, both these methods are time consuming, laborious, wasteful, and thus expensive.

According to this invention there is provided a method of treating a plant to combat disease or pest infestation, such method comprising discharging into the interior of the plant energised droplets of a disease- or pest- combatting liquid from an aerosol generating device containing a propellent.

The invention further provides apparatus for carrying out the above method which includes a pressurised container/valve assembly containing the disease or pest combatting liquid and a propellant and means for connecting the container to the interior of a plant.

Preferably the aerosol is derived from a pressurised container having a spring based nozzle valve at which a stream of aerosol droplets can be obtained, the nozzle being connected to the pipe which is secured as hermetically as possible to that plant interior. The propellant, for example a fluorinated hydrocarbon and any combatting liquid will conveniently be dissolved in a suitable mutual solvent; for example water.

The pressurized container may be secured to the plant by a strap which also serves to hold the nozzle valve in the open condition. Such an arrangement can be set up in a short time by one person and then left unattended for the total usable contents of the container to be supplied to the plant over a period of time. Alternatively, a valve mechanism which can be operated to a stable open position allows this result to be achieved.

During treatment the pressure in the container supplies the aerosol or solution to the plant against the back-pressure provided by the plant.

The back-pressure provided by the plant can also serve to enhance the security of the connection between the tube and the plant, for example by the tube having a sloping annular surface which cooperates with a surrounding wedge-shaped collar which is received in the hole in the plant, such that if the tube endeavours to move out of the hole in the plant then the collar is expanded to become a tighter fit in the hole in the plant.

One embodiment of apparatus for carrying out the method of this invention will now be described by way of example with reference to the drawing which is a diagrammatic sectional side elevation of the apparatus.

As shown the apparatus comprises a container 1 which is pressurised and which contains a chemical compound dissolved in a suitable solvent. The compound/solvent formulation includes a substance which combats pest or disease and an aerosol propellant. The container 1 has a nozzle valve 2 which is spring biased towards the closed condition and by depression of which the pressure in the container 1 can be released to provide a stream of the chemical compound solution.

A tube 3 is connected to the outlet of the valve 2, which tube 3 is received in a hole 4 in a tree 5 to be treated. The tube 3 has a sloping annular surface 3*a* which cooperate with a surrounding wedge-shaped collar 6 which is received in the hole 4, such that if the tube 3 endeavours to leave the hole 4 then the collar 6 is expanded to become a tighter fit in the hole 4. The container 1 is secured to the tree 5 by a strap 7 which passes around the container 1 and the tree 5. The strap 7 holds the container 1 against the tree 5 with sufficient force to maintain the valve 2 open against the action of the spring bias.

The apparatus as above described can be set up by one person, and will thereafter operate to introduce the contents of the container 1 into the tree 5 over a period of time. Not all the contents of the container 1 need be used on a single tree since the container 1 can be removed from the tree at any time, the valve 2 then closing under the spring bias.

It will be appreciated that each droplet produced by a propellant in an aerosol generating device has potential energy. Hence the term "energised" droplets has been used. It is believed that release of this energy assists in the observed and surprising effect that material injected, for example into a tree trunk, is effectively dispersed throughout the trunk. Sap circulation also assists and the method of the invention is advantageously carried out when sap circulation is greatest.

We claim:

1. A method of treating a plant to combat disease or pest infestation comprising the steps of:
   - producing an opening in said plant;
   - inserting a wedge-shaped collar in said opening of the plant;
   - hermetically securing a pipe having an annular sloping plug thereabout in said collar;
   - connecting a pressurized container having a spring biased nozzle valve to said pipe for delivering energized droplets of a liquid to said plant with said spring biased valve compressed against said plant and thereby releasing said energized droplets through said pipe into said plant.

2. Apparatus for treating a plant to combat disease or pest infestation comprising:
   - a pressurized container for holding a disease or pest combatting liquid and a propellant;
   - a spring biased nozzle valve connected to said container;
   - a pipe connected to said valve and having an annular sloping plug provided thereon;
   - a wedge-shaped collar provided on said plug, and to retain said valve in an open condition when said valve is pressed against said plant to be treated, said collar and plug being adapted to hermetically seal said pipe in an opening provided in said plant.

* * * * *